(12) United States Patent
Loussier et al.

(10) Patent No.: US 11,857,587 B2
(45) Date of Patent: Jan. 2, 2024

(54) BIOACTIVE EXTRACT

(71) Applicant: Mycelium Biotech Assets Pty Ltd, Melbourne (AU)

(72) Inventors: Thomas Loussier, Noisy le Roi (FR); Julian Mitchell, Byron Bay (AU)

(*) Notice: Subject to any disclaimer, the term of this patent is extended or adjusted under 35 U.S.C. 154(b) by 425 days.

(21) Appl. No.: 17/151,180

(22) Filed: Jan. 17, 2021

(65) Prior Publication Data

US 2021/0128655 A1 May 6, 2021

Related U.S. Application Data

(63) Continuation-in-part of application No. PCT/AU2019/050752, filed on Jul. 18, 2019.

(30) Foreign Application Priority Data

Jul. 18, 2018 (AU) ................. 2018902593

(51) Int. Cl.
*A61K 36/074* (2006.01)
*A61K 36/185* (2006.01)

(52) U.S. Cl.
CPC .......... *A61K 36/074* (2013.01); *A61K 36/185* (2013.01); *A61K 2236/333* (2013.01)

(58) Field of Classification Search
None
See application file for complete search history.

(56) References Cited

U.S. PATENT DOCUMENTS

2017/0035820 A1  2/2017  Stamets

FOREIGN PATENT DOCUMENTS

| CN | 105902827 A | 8/2016 |
| CN | 107595687 A | 1/2018 |
| WO | 2011057340 A1 | 5/2011 |
| WO | WO2020014745 A1 | 1/2020 |

*Primary Examiner* — Michael V Meller
(74) *Attorney, Agent, or Firm* — Patrick M. Torre; Stites & Harbison PLLC

(57) ABSTRACT

The present invention provides a composition for human or animal consumption, preferably with antiviral, antibacterial, antifungal, antiprotozoal, immune boosting and/or toxin resistance activities. The composition includes a fungal extract component and optionally a fruit extract component. The invention also provides methods for producing the composition and methods of using the composition.

5 Claims, 2 Drawing Sheets

Average honey bee lifespan in a group fed with a Control solution (Control group) vs. a group fed with extract at 1.5 % (Group 3)

BIOACTIVE EXTRACT

This application is a continuation-in-part of International Application PCT/AU2019/050752, filed Jul. 18, 2019, the disclosure of which is incorporated herein by reference, and also claims the priority of Australian Patent App. Ser. No. 2019902593, filed Jul. 18, 2018, the disclosure of which is incorporated herein by reference. International Application PCT PCT/AU2019/050752, to which this application claims priority under 35 USC 120, contains a certified copy of Australian Patent App. Ser. No. 2019902593.

FIELD OF THE INVENTION

The present invention relates to a composition including fungal extract components from one or more medicinal fungal species, and methods for producing the composition. Preferably, the fungal extract components are combined with a fruit extract to provide the composition. More particularly, the composition may have antiviral, antibacterial, antifungal, antiprotozoal and/or immune boosting activities.

BACKGROUND OF THE INVENTION

Antibiotic resistance is one of the most pressing public health problems currently faced in today's society. Antibiotic resistance in children and older adults is of particular concern because these age groups have the highest rates of antibiotic use.

Antibiotic resistance can cause significant suffering for people who have common infections that once were easily treatable with antibiotics. When antibiotics fail to treat infections, the infections often last longer, resulting in more severe illness and increased burden upon the health care system through patients requiring additional visits to health care professionals or longer hospital stays.

Agriculture industries are another key area affected by the development of bacterial antibiotic resistance. In particular, large scale animal production for human food consumption, due to its high concentration of animals per square metre and confined space, provides an ideal environment for pathogen incubation.

Overuse and misuse of antibiotics within both the human health and agriculture industries threatens the usefulness of these important drugs. One of the major contributors to misuse of antibiotics, and therefore antibiotic resistance, is compliance within both the health and agriculture fields.

In addition, a major difficulty in the development of novel antimicrobial and antiviral agents is an inherent toxicity towards the host organism. For example, a novel antibacterial that destroys harmful microorganisms but also harms the animal host or its naturally occurring biota is neither medically practical to the health community nor commercially attractive to the agricultural community.

It is an object of the present invention to overcome, or at least alleviate, one or more of the difficulties or deficiencies associated with the prior art.

SUMMARY OF THE INVENTION

In one aspect, the present invention provides a method of producing a composition, said method including the steps of:
providing
a sample from one or more fungal species,
an aqueous solvent, and
an alcohol;
extracting one or more soluble compounds from the fungal sample using the aqueous solvent to produce an aqueous mycelia extract;
precipitating one or more soluble compounds from the fungal extract using the alcohol; and
removing the resulting precipitate from the supernatant to provide the composition.

In a preferred embodiment, the extracting process is fermentation.

Preferably, the aqueous solvent in the extraction process is a mixture of water and an alcohol.

In a particularly preferred embodiment, one or more soluble compounds from the fungal sample is extracted using fermentation, wherein the aqueous solvent used to produce an aqueous mycelia extract is a mixture of water and an alcohol.

Preferably, the fungal sample used in the extraction is selected from the mycelia and the fruiting body of the fungal species. In a particularly preferred embodiment, the fungal sample used in the extraction method is the mycelia.

In a preferred embodiment, the method includes the further step of providing a fruit extract and combining the supernatant with the fruit extract to provide the composition. In a particularly preferred embodiment, the method includes the further step of providing a fruit extract before the extraction step.

Preferably, the composition of the present invention has antiviral, antibacterial, antifungal, antiprotozoal, toxin resistance and/or immune boosting activities.

In an alternative preferred embodiment, the supernatant is filtered prior to addition of the fruit extract.

Preferably, the supernatant is filtered through a filter having a pore size between approximately 0.05 and 0.5 μm, more preferably between approximately 0.1 and 0.3 μm, most preferably between approximately 0.12 and 0.2 μm, prior to addition of the fruit extract.

The fungal species of the present invention may be of any suitable type. In a preferred embodiment, the fungal species is a medicinal fungal species. In an alternatively preferred embodiment, the fungal species may belong to the group of fungi known as polypores. Even more preferably the fungal species may be of the genus *Ganoderma*.

By 'medicinal fungal species' used herein is meant a fungal species which has been shown to produce compounds or metabolites which are known to be pharmacologically active.

In a more preferred embodiment, the medicinal fungal species may be selected from the group consisting of a *Ganoderma* spp, *Fomitopsis officinalis*, *Inonotus obliquus*, *Fomes fomentarius*, *Trametes versicolor*, *Pleurotus djamor*, *Pleurotus eryngii*, *Ophiocordyceps sinensis*, *Hypsizygus ulmarius*, *Hericium erinaceus*, *Pleurotus ostreatus*, *Lentinus edodes*, *Hericium coralloides*, *Stropharia rugoso-annulata*, *Agrocybe aegerita*, *Auricularia* spp., *Boletus edulis*, *Cantharellus cibarius*, *Coprinus comatus*, *Craterellus cornucopioides*, *Flammulina* spp., *Hydnum repandum*, *Lactarius deliciosus*, *Lyophyllum* spp., *Marasmius oreades*, *Morchella* spp., *Pholiota nameko*, *Tremella* spp., *Tricholoma bakamatsutake*, *Tricholoma caligatum*, *Tricholoma matsutake*, *Tricholoma magnivelare*, *Tricholoma terreum*, *Volvariella volvacea*

In a further preferred embodiment, the medicinal fungal species may be selected from the group consisting of *Ganoderma applanatum*, *Ganoderma resinaceum*, *Ganoderma lucidium* and variants thereof.

In a further preferred embodiment, the medicinal fungal species is selected from the group consisting of *Ganoderma lucidium* and variants thereof, more particularly *Ganoderma lucidium*, var. *G resinaceum*.

In a particularly preferred embodiment, the medicinal fungal species may be *Ganoderma lucidium*.

Preferably, the fungal species of the present invention may be isolated or substantially purified prior to preparation of mycelia therefrom. By 'substantially purified' is meant that the fungus is free of other organisms. The term therefore includes, for example, a fungus in axenic culture. Preferably, the fungus is at least approximately 90% pure, more preferably at least approximately 95% pure, even more preferably at least approximately 98% pure.

The term 'isolated' means that the fungus is removed from its original environment (e.g. the natural environment if it is naturally occurring). For example, a naturally occurring fungus present in a living plant is not isolated, but the same fungus separated from some or all of the coexisting materials in the natural system, is isolated.

The fungus may be cultured to produce the mycelia. This may include growing the fungus in a culture medium including a source of carbohydrates. For example, the culture medium may be a grain such as wheat. Thus, in a preferred embodiment, the mycelia may be present in a grain. The grain may be selected from the group consisting of rice, rye, wheat, barley and oat. In a preferred embodiment, the grain may be wheat.

In an alternative embodiment, the culture medium may be a liquid, such as a nutrient enriched fermentation liquid medium. Thus in a preferred embodiment, the mycelia may be present in liquid state. The nutrients may be selected from the group consisting of nutritional yeast, vitamins, carbohydrates, starch and minerals.

The fungus may be cultured in dark and/or light conditions. For example, the fungus may be cultured in continual darkness, or under a regime of approximately 12 hours dark and approximately 12 hours light, or under a regime of approximately 12 hours darklight and approximately 12 hours dark. Preferably, the fungus is cultured in continual darkness.

The fungus may also be cultured under conditions of constant temperature, or under conditions of a range of temperatures. Preferably, the fungus is cultured at room temperature.

Fungal mycelia may be cultivated via a solid state fermentation to obtain the spawn or mycelium grown on grain. For example the fungus may be cultured in a liquid culture medium to create the $1^{st}$ spawn generation which may be used to inoculate a grain to produce the $2^{nd}$ spawn generation. Preferably this process is repeated at least once to achieve subsequent spawn generations.

Alternatively, inoculation of the grain may be performed by exposing the grain to a solid inoculated medium such as a colonised agar plate.

In an alternative embodiment, fungal mycelia may be cultivated via a liquid state fermentation. For example, the fungus may be cultured in a liquid culture medium to create the $1^{st}$ mycelium generation which may be use to inoculate a larger fermentation vessel to produce the $2^{nd}$ mycelium generation. Preferably this process is repeated at least once to achieve subsequent mycelium generations.

Alternatively, inoculation of the liquid may be performed by exposing the liquid to a solid inoculated medium such as a colonised agar plate.

The fungal mycelia may be cultured for a period of approximately 1 to 120 days, more preferably from approximately 10 to 120 days, more preferably from approximately 20 to 120 days.

While applicant does not wish to be restricted by theory, mycelial extracts are preferred to "mushroom fruiting body extracts" because it is thought that the hyphae produce extracellular exudates that are rich in accessible water, oils, polysaccharides, amino acids, B vitamins, coumarins, p-coumaric acids, phenols and/or polyphenols, as well as ergosterols, enzymes, acids, including fatty acids, antibacterials and/or antivirals. Interestingly, many of the grains preferred for mycelial spawn production for mushroom industry are also rich sources of p-coumaric acids and may be useful in bee attractant compositions. The primary phenolic acids in rice grain were identified as p-coumaric acid, ferulic acid, and sinapinic acid.

The aqueous solvent may be of any suitable type. By "aqueous solvent" as used herein is meant a water based solvent or a solvent including at least approximately 50% water, preferably distilled water. In a preferred embodiment, the aqueous solvent is water, preferably distilled water.

In a more preferred embodiment, the aqueous solvent employed in the method of the present invention may be heated. Preferably the aqueous solvent may be heated to a temperature between approximately 70° C. and 100° C., more preferably 80° C. and 95° C., more preferably approximately 90° C.

In a further preferred embodiment, the extraction may be carried out for a period of between approximately 10 days and 80 days, more preferably between approximately 15 days and 45 days, even more preferably between approximately 20 days and 35 days.

In a particularly preferred embodiment the one or more soluble compounds may be extracted from the mycelia by boiling the mycelia in the aqueous solvent.

In a particularly preferred embodiment the one or more soluble compounds may be extracted from the mycelia by fermenting the mycelia in a solvent mixture of water and ethanol.

The precipitation process employed in the method of the present invention may be performed by any suitable method, provided that it results in the undesired components of the mycelia extract becoming insoluble. Preferably an alcohol is used to precipitate the undesired components.

In a preferred embodiment, the alcohol employed in the method of the present invention may be selected from the group consisting of ethanol, isopropanol, methanol, butyl alcohol or any other C2-C6 alcohol.

In a particularly preferred embodiment, the alcohol may be ethanol, more preferably ethanol-95.

In a further preferred embodiment, the alcohol may be an alcohol diluted to a concentration between approximately 10% and 60% v/v, more preferably approximately 20% to 50% v/v, even more preferably approximately 25% to 45% v/v.

In an alternative embodiment, the alcohol may optionally be added to the myceliated grain prior to addition of the aqueous solvent.

The separation process employed in the method of the present invention may be performed by any suitable method, provided that it separates the resulting precipitate from the supernatant. Suitable separation processes will be apparent to the person skilled in the art, for example filtration.

In a preferred embodiment, the filtration process may be ultrafiltration. For example, a semi-permeable membrane may be used. Alternatively, a tubular centrifuge may be used.

In a preferred embodiment, the composition of the present invention comprises the supernatant, with most or substantially all of the precipitate removed. Preferably, at least approximately 90%, more preferably at least approximately 95%, even more preferably at least approximately 98% of the precipitate is removed.

In a preferred embodiment, the fungal extract may include one or more organic compounds.

By an 'organic compound' is meant a chemical compound, the molecules of which contain the element carbon. In a preferred embodiment, the organic compound may be a hydrocarbon. By a 'hydrocarbon' is meant an organic compound containing, inter alia, the elements carbon and hydrogen.

In a particularly preferred embodiment, the fungal extract may include one or more organic compounds. Preferably, the one or more organic compounds are selected from the group consisting of polysaccharides, triterpenoids, complex sugars, antivirals, antibacterials, families of coumarins (a group of polyphenolic compounds, colourless and crystalline phytochemical substances), cytochrome p450 up-regulating coumaric acids (antioxidant protection by p-coumaric acid), essential amino acids (for example, histidine, isoleucine, leucine, lysine, methionine, phenylalanine, threonine, tryptophan, and valine) and other amino acids such as aspartic acid, serine, glutamic acid, glycine, arginine, alanine, proline, tyrosine, hydroxyproline, taurine. Furthermore, polyphenols, beta glucans and vitamins, such as vitamin B3, may also be present.

In a more preferred embodiment, the fungal extract may include compounds selected from the group consisting of p-coumaric acids, proteins, polysaccharides, triterpenoids, phenolics acids, amino acids, coumarins, and beta glucans.

In a further preferred embodiment, the supernatant may be combined with a fruit extract, preferably a fruit extract from the fruit of a plant native to Australia, to provide the composition of the invention. More preferably, the fruit extract is an Australian native indigenous bush food whole fruit body extract. More preferably the fruit extract is an extract of the fruit of *Terminalia* species, even more preferably an extract from the fruit of *Terminalia ferdinandiana*.

Preferably the fruit extract is a powder fruit extract. More preferably, the powder fruit extract may be diluted, for example in an aqueous solution, prior to combination with the mycelia extract.

In a particularly preferred embodiment, the fruit extract is combined with the mycelial extract at a ratio of between approximately 1:70 and 1:10 relative to the myceliated grain used in the described extraction.

In a preferred embodiment, the fruit extract is combined with the mycelial extracts and the fruiting body extracts at a ratio of between approximately 1:70 and 1:10 relative to the mycelium and fruiting bodies used in the described extraction.

In a further aspect of the present invention, there is provided a composition produced by the methods of the present invention. Preferably, the composition of the present invention has antiviral, antibacterial, antifungal, antiprotozoal and/or immune boosting activities.

In a still further aspect of the present invention, there is provided a composition for human or animal consumption, said composition including a fungal extract component and a fruit extract component.

In an alternatively preferred embodiment, there is provided a composition suitable for human or animal consumption, said composition including a fungal extract component and a fruit extract component, wherein the composition is lyophilised to form a powder.

For example, freeze dried mycelium powder from wheat myceliated grain may be use to feed animals such as cattle, birds and pigs.

Preferably, the fungal extract component includes the supernatant having undergone precipitation with an alcohol. Preferably, at least approximately 90%, more preferably at least approximately 95%, even more preferably at least approximately 98% of the precipitate is removed from the supernatant following alcohol precipitation.

Preferably the fruit extract is an extract from the fruit of a plant native to Australia as hereinbefore described. More preferably the fruit extract is an extract of the fruit of *Terminalia* species, even more preferably an extract from the fruit of *Terminalia ferdinandiana*.

Preferably the fruit extract is a powder fruit extract. More preferably, the powder fruit extract may be diluted, for example in an aqueous solution, prior to combination with the mycelia extract.

In a particularly preferred embodiment, the fruit extract is combined with the fungal extract at a ratio of between approximately 1:70 and 1:10 relative to the myceliated grain used in the described extraction.

In a preferred embodiment, the fruit extract is combined with the mycelial extracts and the fruiting body extracts at a ratio of between approximately 1:70 and 1:10 relative to the mycelium and fruiting bodies used in the described extraction.

Preferably, the composition of the present invention has antiviral, antibacterial, antifungal, antiprotozoal, toxin resistance and/or immune boosting activities.

In a preferred embodiment, the composition of the present invention may have antiviral and/or immune enhancing effects from extracts from pure cultured mycelium, optionally diluted to within specific ranges, which offer benefits to insects, such as bees, and other animals, including humans.

While Applicant does not wish to be restricted by theory, the compositions of the present invention are also thought to be rich in compounds that up-regulate genes for detoxification and defence against pollutants, pesticides and pathogens in animals, including humans and bees. Thus, compositions (e.g. honeys) including these fungal components could proffer medicinal benefits to bees and other animal species, including humans.

While Applicant does not wish to be restricted by theory, the compositions of the present invention may contain polyphenols, and more particularly coumarins, which help activate p450 enzyme pathways, which in turn help animals such as bees detoxify endogenous, foreign, natural and anthropogenic toxins and lessen their associated deleterious effects.

While Applicant does not wish to be restricted by theory, it is thought that the fungal extracts modulate, induce and/or increase the expression of detoxification and/or xenobiotic metabolizing genes, specifically to up-regulate detoxification genes, increase midgut metabolism of pesticides, function as a nutraceutical regulating immune and/or detoxification processes, up-regulate immune, metabolic and/or nutrient pathways (for example, lipid and/or glucose-metabolizing pathways) and/or up-regulate genes encoding antimicrobial peptides. P-coumaric acid, being more soluble in ethanol than water, is richer in the ethanolic extracted supernatant. The ethanolic supernatant, with concentrated p coumaric acids, is a reservoir of bee-beneficial p450 coding compounds.

While applicant does not wish to be restricted by theory, it is thought that due to polysaccharides (in particular b-D-glucans), proteins, and/or triterpenoids, the composition of the present invention has an immunomodulating effect. These active substances are involved in the mitogenicity and activation of immune effector cells, such as T cells, macrophages, and natural killer cells, resulting in the production of cytokines, including interleukins, tumour necrosis factor-d, and interferons. b-D-glucans induce a biological response by binding to membrane complement receptor type 3 (CR3, $a_M b_2$ integrin, or CD11b/CD18) on immune effector cells. The ligand-receptor complex may be internalized and activate nuclear factor NF-kB.

Accordingly, the present invention provides a method of treating preventing or reducing viral, bacterial, fungal and/or protozoal infections in an animal in need thereof, said method including administering to said animal an effective amount of a composition according to the present invention.

By "an effective amount" is meant an amount sufficient to produce a measurable antiviral, antibacterial, antifungal or antiprotozoal effect in the animal. Such amounts can be readily determined by an appropriately skilled person, taking into account the type of animal, the route of administration and other relevant factors. Such a person will readily be able to determine a suitable amount and method of administration.

The present invention also provides a method of increasing immune activity in an animal in need thereof, said method including administering to said animal an effective amount of a composition according to the present invention.

By "an effective amount" is meant an amount sufficient to produce a measurable increase in immune response in the animal. Such amounts can be readily determined by an appropriately skilled person, taking into account the type of animal, the route of administration and other relevant factors. Such a person will readily be able to determine a suitable amount and method of administration.

The present invention also provides a method of increasing resistance to toxins in an animal in need thereof, said method including administering to said animal an effective amount of a composition according to the present invention.

By "an effective amount" is meant an amount sufficient to produce a measurable increase in resistance to toxins in the animal. Such amounts can be readily determined by an appropriately skilled person, taking into account the type of animal, the route of administration and other relevant factors. Such a person will readily be able to determine a suitable amount and method of administration.

In a preferred embodiment, the toxins may be endogenous, foreign, natural and/or anthropogenic toxins. In a particularly preferred embodiment, the toxins may be pollutants and/or pesticides.

The present invention also provides use of fungal extracts in the manufacture of a medicament for the treatment of viral, bacterial, fungal and/or protozoal infections in an animal.

The present invention also provides use of fungal extracts in the manufacture of a medicament for increasing immune activity in an animal.

The present invention also provides use of fungal extracts in the manufacture of a medicament for increasing resistance to toxins in an animal.

Preferably, the fungal extracts include fungal extract components as hereinbefore described. More preferably the fungal extract components are combined with a fruit extract as hereinbefore described in the manufacture of the medicament. In a further preferred embodiment, the manufactured medicament is lyophilised prior to being administered.

Preferably, the fungal extract component includes the supernatant having undergone precipitation with an alcohol. Preferably, at least approximately 90%, more preferably at least approximately 95%, even more preferably at least approximately 98% of the precipitate is removed from the supernatant following alcohol precipitation.

In a preferred embodiment, the animal may be an insect. In a particularly preferred embodiment, the insect may be a bee.

In a preferred embodiment, the animal may be a mammal. In a particularly preferred embodiment, the mammal may be a human.

In a further aspect, the present invention provides a method of treating preventing or reducing viral, bacterial, fungal and/or protozoal infections in a human in need thereof, said method including administering to said human an effective amount of a composition according to the present invention.

In a further aspect, the present invention provides a method of increasing immune activity in an human in need thereof, said method including administering to said human an effective amount of a composition according to the present invention.

In a still further aspect, the present invention provides a method of increasing resistance to toxins in an human in need thereof, said method including administering to said human an effective amount of a composition according to the present invention.

The present invention will now be more fully described with reference to the accompanying Examples and drawings. It should be understood, however, that the description following is illustrative only and should not be taken in any way as a restriction on the generality of the invention described above.

BRIEF DESCRIPTION OF THE DRAWING/FIGURES

DETAILED DESCRIPTION OF THE EMBODIMENTS

Figure 1:
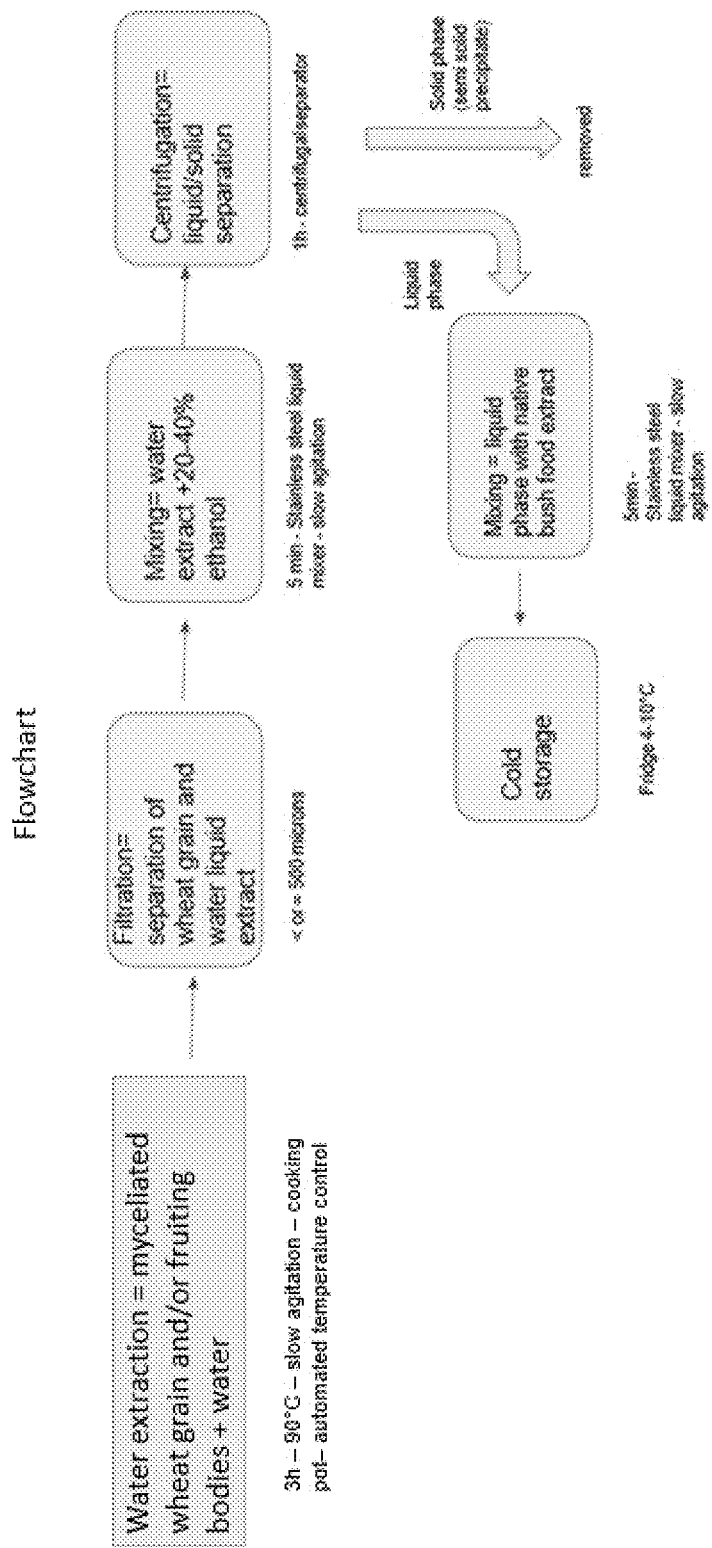
FIG. 1 shows the production process employed to produce the bioactive extract product described in this application.

The present invention is based on a biotechnology developed solution to support the immune system of animals and humans, obtained by the combination of a double liquid extract of mycelia of a medicinal fungal species (*Ganoderma lucidium*, var. *G. resinaceum*) and a native Australian bush food Kakadu plum (*Terminalia ferdinandiana*). This designed fungal medicinal immune boosting solution helps tilt the balance in favour of a natural antibacterial, antifungal, antiprotozoal and immune support biotechnology solution as a natural alternative to antibiotics and other costly synthetic drugs commonly used to improve health and maintain immunity.

Firstly, the soluble compounds (polysaccharides mainly) and alcohol soluble compounds (triterpenoids mainly) are extracted by fermenting the mycelium and fruiting bodies over a several days using an aqueous alcoholic solution.

The native Australian bush food extract is added to the extraction-fermentation process. While applicant does not wish to be restricted by theory, it is thought that the mycelia and Kakadu plum extract contains one or more of the following compounds:

polyphenols (coumarins), p-coumaric acids, elagic and gallic acid, magnesium, zinc, riboflavin (vit B2), niacin equivalents (vitamin B3) and vitamin C (ascorbic acid), calcium, potassium, sodium, iron, phosphorous, manganese, copper and molybdenum, dietary fibers.

Example 1—Preparation of Myceliated Wheat Grain

The mycelium is cultivated via a liquid state fermentation to mycelium extractable culture. Firstly, a pure culture of mycelium grown on agar tube MEA (Malt Extract Agar) medium or liquid culture syringe is used to inoculate the 1st mycelium generation G1 on agar plate. Once the agar plate is fully colonised (10-14 days), this 1st generation is used to inoculate a 20 litre mycelium bioreactor with nutrient solutions to create the 2nd mycelium generation G2. Finally, after the bioreactor is fully colonised by the mycelium (14 days), it is used to inoculate a 1000 litre mycelium bioreactor which constitutes the 3rd mycelium generation G3. Liquid inoculation is preferred for liquid fermentation in the bioreactor, although inoculation with colonized agar may be utilized, and inoculation with colonized grain is preferred for sawdust or wood chip substrates. When the mycelium reaches a dense mass of growth (preferably after 20 but before 120 days growth in fermentation or in solid state fermentation subsequent to inoculation, but well before fruit body formation) mycelial mass can be extracted with additional alcohol.

Example 2—Extraction 30 g of ethanol, 70 g of mushroom fruiting bodies and 10 g of fruit extract are added to 70 g of an aqueous solution of fermented mycelium to form a mixture. The mixture is heated to a temperature of approx. 100° C. The temperature of the mixture is maintained at 100° C. for approximately 7 days. The mixture is then cooled to room temperature and filtered to remove the remaining solid matter. The resulting solution is stored at approx. 4° C.

Example 3—Addition of the Kakadu Plum Powder Extract

The isolated supernatant containing the mycelial extract in a 1 L aqueous alcohol solution is filtered and mixed with 50 g of kakadu plum powder extract which is mixed with a syrup mixer such as a double cone mixer, double arm mixer, kneader mixer, ribbon blenders, ploughshare mixer and other mixers adapted to liquids.

Example 4—Combination of Extracts

Whilst Applicant does not wish to be restricted by theory, one or more of the antiviral, antibacterial, antifungal and antiprotozoal molecules and their analogs described in the liquid double mycelium extract may be combined with the water liquid kakadu plum extract molecules to provide a dual, synergistic benefit for reducing viruses and/or up-regulation of immune system pathways, resulting in the cumulative benefit of reducing viral-bacterial-fungal and protozoal burdens.

Kakadu plum extract is rich in riboflavin (vit B2), niacin equivalents (vitamin B3) and vitamin C (ascorbic acid). These two vitamins act as coenzymes in hundreds of redox reactions and more particularly in the detoxification pathway (take place in the liver) where they act as cofactors (vit B3 and B2) and antioxidant (vit C). The main actors of the phase I of the liver detoxification pathway are composed of the cytochrome P450 enzymes which involved 57 genes in humans.

Kakadu plum extract also contains gallic acid, which contains antibacterial, antiviral, antifungal, anti-inflammatory, anti-tumor, anti-mutagenic and anti-bronchodilatory properties. Ellagic acid shows anti-carcinogenic effects to maintain healthy human tissues.

Kakadu plum is found naturally in open woodland across Northern Australia, namely in the Kimberley region of Western Australia, the Northern Territory and Queensland. Following a period of oversupply, the market is currently undersupplied with demand steadily increasing. Production is estimated to average 15-17 tonnes per annum.

As previously described, the polyphenols (mainly coumarins) and phenolic acids (p-coumaric acid mainly) found in mycelium extract activate the P450 enzymes pathways and thus lead to detoxification of endogenous, foreign, natural and anthropogenic toxins.

Thus, the synergistic effect of the activation of the cytochrome p450 enzymes by the polyphenols found in mycelium extract and the co-factors Vit C, B3 and B2 found in kakadu plum extract, result in the cumulative health benefit at a molecular level.

Example 5—Honey Bee

Honey bees (bees) from three different colonies are placed in an incubator at 33° C. and 60% relative humidity for approximately 48 hours. 30 bees from the incubator are transferred into an enclosure. 40 enclosures are filled with bees, with 30 bees per enclosure. The enclosures are randomly distributed into four experimental groups. The experimental groups are as follows:

1. Control (1:1 sugar syrup solution)
2. 0.5% extract (v/v) in a 1:1 sugar syrup solution
3. 1.5% extract (v/v) in a 1:1 sugar syrup solution
4. 2.5% extract (v/v) in a 1:1 sugar syrup solution The groups describe the type of food fed to each group of bees, ad libitum. The 'extract' is the extract of mycelia of a medicinal fungal species as describes above. The sugar syrup solution (Control solution) is prepared using 50% (w/w) sugar in water.

The enclosures containing the bees are kept in a dark room at 33° C. and 60% relative humidity. Bee mortality is monitored every 2-3 days. The food is replaced every 2-3 days.

Bees in experimental group 1 (Control group) show an average lifespan of 17.68 days. Bees in experimental groups 2 and 4 maintained an average lifespan of 17.68 days.

Figure 2:
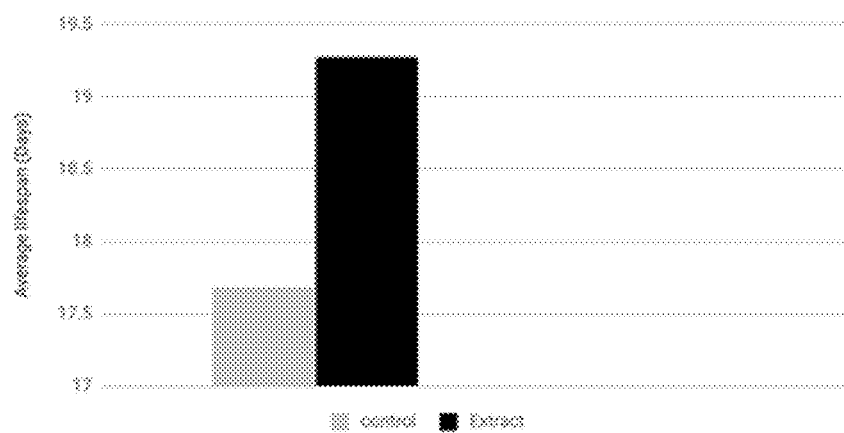
FIG. 2 shows the average honey bee lifespan in a group fed with a Control solution (Control group) vs. a group fed with extract at 1.5% (Group 3).

Bees in experimental group 3 show an average lifespan of 19.27 days. More specifically, the use of the extract at 1.5% (Group 3) show an increase in honey bee longevity by 8.25% compared to the Control group. Refer to FIG. 2. Overall the use of the extract at 1.5% significantly increases the average lifespan of the bee, when compared to the Control group.

Finally, it is to be understood that various alterations, modifications and/or additions may be made without departing from the spirit of the present invention as outlined herein.

The invention claimed is:

1. A method of producing a composition, consisting essentially of:

a) providing a sample from the mycelia of a medicinal fungal species grown on rice, wheat, barley, or oats, wherein the medicinal fungal species is selected from the group consisting of a *Ganoderma* spp, *Fomitopsis officinalis, Inonotus obliquus, Fomes fomentarius, Trametes versicolor, Pleurotus djamor, Pleurotus eryngii, Ophiocordyceps sinensis, Hypsizygus ulmarius, Hericium erinaceus, Pleurotus ostreatus, Lentinus edodes, Hericium coralloides, Stropharia rugoso-annulata, Agrocybe aegerita, Auricularia* spp., *Boletus edulis, Cantharellus cibarius, Coprinus comatus, Craterellus cornucopioides, Flammulina* spp., *Hydnum repandum, Lactarius deliciosus, Lyophyllum* spp., *Marasmius oreades, Morchella* spp., *Pholiota nameko, Tremella* spp., *Tricholoma bakamatsutake, Tricholoma caligatum, Tricholoma matsutake, Tricholoma magnivelare, Tricholoma terreum*, and *Volvariella volvacea*;

b) extracting one or more soluble compounds from the sample using an aqueous solvent to yield an aqueous fungal extract;

c) precipitating one or more soluble compounds from the aqueous fungal extract using ethanol to yield a precipitated extract;

d) removing the resulting precipitate from the precipitated extract to leave a supernatant; and e) combining the supernatant with Kakadu plum powder to yield the composition.

2. The method according to claim 1, wherein the medicinal fungal species is selected from the group consisting of *Ganoderma applanatum, Ganoderma resinaceum*, and *Ganoderma lucidium*.

3. The method according to claim 2, wherein the medicinal fungal species is *Ganoderma lucidium*.

4. The method according to claim 1, wherein the ethanol is diluted to a concentration of between approximately 10% and 60%.

5. The method according to claim 1, wherein the composition has antiviral, antibacterial, antifungal, antiprotozoal, immune boosting and/or toxin resistance activities.

* * * * *